United States Patent
Lattner et al.

(10) Patent No.: US 8,344,197 B2
(45) Date of Patent: Jan. 1, 2013

(54) PRODUCTION OF PARA-XYLENE BY THE METHYLATION OF BENZENE AND/OR TOLUENE

(75) Inventors: James R. Lattner, La Porte, TX (US); Mark P. Hagemeister, Houston, TX (US); Jon Edmond Randolph Stanat, Westhampton Beach, NY (US); John Di-Yi Ou, Houston, TX (US); Xiaobo Zheng, Houston, TX (US); Lu Han, Herndon, VA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 289 days.

(21) Appl. No.: 12/894,778

(22) Filed: Sep. 30, 2010

(65) Prior Publication Data

US 2011/0092755 A1 Apr. 21, 2011

Related U.S. Application Data

(60) Provisional application No. 61/253,732, filed on Oct. 21, 2009.

(51) Int. Cl.
*C07C 2/66* (2006.01)
(52) U.S. Cl. ......... 585/467; 585/469; 585/446; 585/911
(58) Field of Classification Search .................. 585/467, 585/469, 446, 911
See application file for complete search history.

(56) References Cited

U.S. PATENT DOCUMENTS

| | | | |
|---|---|---|---|
| 3,965,207 A | 6/1976 | Weinstein | |
| 4,670,616 A | 6/1987 | De Simone et al. | |
| 6,388,156 B1 | 5/2002 | Ou et al. | |
| 6,504,072 B1 | 1/2003 | Brown et al. | |
| 6,642,426 B1 | 11/2003 | Johnson et al. | |
| 7,387,978 B2 | 6/2008 | Wu et al. | |

OTHER PUBLICATIONS

A.K. Aboul-Gheit et al.,"*Catalytic Para-Xylene Maximization. V. Toluene Methylation with Methanol and Disproportionation of Toluene Using Pt/ZSM-5 and Pt/Mordenite Catalysts*", Journal of the Chinese Chemical Society, vol. 51, pp. 817-826 (2004).

*Primary Examiner* — Thuan D Dang
(74) *Attorney, Agent, or Firm* — Andrew B. Griffis

(57) ABSTRACT

In a process for the production of para-xylene, methanol is preheated to a first temperature, an aromatic feedstock comprising toluene and/or benzene is preheated to a second temperature and the preheated methanol and aromatic feedstocks are fed to a reactor at a first methanol to aromatic feedstock molar ratio. The preheated aromatic feedstock is contacted with the preheated methanol under alkylation conditions in the reactor in the presence of a catalyst so that the methanol reacts with the aromatic feedstock to produce an effluent comprising para-xylene. During the reaction, a temperature is measured within the reactor and is compared with a predetermined optimal temperature. The methanol to aromatic feedstock molar ratio is then adjusted in a manner to reduce any difference between the measured and predetermined optimal temperatures in the reactor.

13 Claims, No Drawings

PRODUCTION OF PARA-XYLENE BY THE METHYLATION OF BENZENE AND/OR TOLUENE

CROSS REFERENCE TO RELATED APPLICATIONS

This application claims the benefit of Provisional Application No. 61/253,732, filed Oct. 21, 2009, the disclosure of which is incorporated by reference in its entirety.

FIELD

This invention relates to a process for producing para-xylene by the selective methylation of benzene and/or toluene.

BACKGROUND

Para-xylene is an important starting material for manufacturing terephthalic acid, which is itself a valuable intermediate in the production of synthetic polyester fibers, films, and resins. These polyester materials have many practical, well known uses, such as in fabrics, carpets, and apparel.

One known route for the manufacture of para-xylene is by the methylation of benzene and/or toluene. For example, U.S. Pat. No. 6,504,072 discloses a process for the selective production of para-xylene which comprises reacting toluene with methanol under alkylation conditions in the presence of a catalyst comprising a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa) wherein said porous crystalline material has undergone prior treatment with steam at a temperature of at least 950° C. to adjust the Diffusion Parameter of said material to about 0.1-15 $sec^{-1}$. The reaction can be carried out in a fixed, moving, or fluid catalyst bed.

Although the reaction of toluene and methanol, particularly using the highly steamed catalyst described in the '072 patent, is selective to the production of para-xylene, in commercial applications it is critical to maximize product selectivity and feedstock utilization. Thus, competing reactions include reaction of methanol with itself to produce light paraffins and olefins and coke, which reactions involve loss of valuable methanol feed. There is therefore considerable interest in developing methods to further enhance the selectivity of the benzene/toluene methylation process.

For example, U.S. Pat. No 6,642,426 discloses production of xylene by fluidized bed alkylation of toluene with methanol, in which improved conversion and selectivity is realized when the methanol is injected in stages into the fluidized bed at one or more locations downstream from the location of aromatic reactant introduction into the fluidized bed. In addition, the '246 patent teaches that methanol utilization is enhanced by using a molar excess of the aromatic feed as compared to the methanol feed.

Another important parameter in the reaction of benzene and/or toluene with methanol to produce para-xylene is temperature, with relatively high temperatures, typically between 450° C. and 700° C., being required to maximize conversion. As a result, the aromatic and methanol feeds are preheated before being supplied to the alkylation reactor(s), with the exothermic heat generated by the alkylation reaction generally being sufficient to maintain the reaction temperature at the desired value. In practice, however, there are limits on the temperatures to which the different feeds can be preheated.

For example, in the case of the benzene/toluene feed, the preheating temperature is limited by the coking rates in the preheater which, depending on factors such as heat flux, stream composition and heat transfer surface metallurgy, will generally be about 550° C. In the case of the methanol feed, decomposition to carbon oxides, hydrogen and methane will generally limit the preheating temperature to about 220° C.

In a conventional reactor system, the feed rates of the methanol and aromatic feeds and the molar ratio of aromatic to methanol are set at the desired values and the reaction temperature is controlled by adjusting the amount of heat supplied to feeds in the preheaters. However, this approach suffers from a problem in that, for a given molar ratio of aromatic to methanol, it may not be possible to achieve the optimal reaction temperature before the maximum feed preheating constraints are reached. This will result in the methylation reaction being operated at a temperature less than that required for maximum selectivity to the desired para-xylene product.

According to the invention, this problem is addressed by maintaining the preheating temperatures of the methanol and aromatic feeds at or near their desired maximum values and then adjusting the molar ratio of the methanol to aromatic feeds to achieve the desired reaction temperature. For example, since the conversion of methanol in the process, whether by alkylation or production of light gases, is exothermic, an increase in the methanol to aromatic molar ratio can be used to increase the supply of heat to the reaction and hence raise the reaction temperature. Alternatively, since conversion of methanol is the rate limiting step, a decrease in the methanol to aromatic molar ratio can be used to decrease the supply of heat to the reaction and hence lower the reaction temperature. Controlling the reaction temperature in this manner guarantees that, for a given desired reaction temperature and maximum value of the feed preheating temperatures, the lowest possible methanol to aromatic molar ratio will be employed. This maintains the methanol concentration in the reactor at its lowest possible value, resulting in the highest possible selectivity to the desired xylene product.

SUMMARY

In one aspect, the invention resides in a process for the production of para-xylene by reacting methanol with an aromatic feedstock comprising toluene and/or benzene, the process comprising:

(a) preheating the methanol to a first temperature;

(b) preheating the aromatic feedstock to a second temperature;

(c) supplying the preheated methanol and the preheated aromatic feedstock to a reactor;

(d) contacting said preheated aromatic feedstock with said preheated methanol under alkylation conditions in said reactor in the presence of a catalyst so that the methanol reacts with the aromatic feedstock to produce an effluent comprising para-xylene;

(e) measuring a temperature within said reactor and comparing the measured temperature with a predetermined optimal temperature; and (f) adjusting the molar ratio of methanol to aromatic feedstock supplied to the reactor in (c) in a manner to reduce any difference between the measured and predetermined optimal temperatures in the reactor.

Conveniently, the methanol to aromatic feedstock molar ratio is adjusted to reduce the difference between the measured and predetermined optimal temperatures in the reactor to less than 10° C., such as less than 5° C.

Conveniently, said adjusting comprises increasing said methanol to aromatic feedstock molar ratio if the measured temperature is less than said predetermined optimal temperature and comprises decreasing said methanol to aromatic feedstock molar ratio if the measured temperature is greater than said predetermined optimal temperature.

Conveniently, said first temperature is between about 150° C. and about 300° C., such as about 220° C.

Conveniently, said second temperature is between about 300° C. and about 700° C., such as about 550° C.

Conveniently, said predetermined optimal temperature is between about 450° C. and about 700° C., such as about 590° C.

In one embodiment, said alkylation conditions are adiabatic, that is heat is not actively added to or removed from the reactor.

Conveniently, the amount and/or the activity of the catalyst contacting said preheated aromatic feedstock and said preheated methanol in (d) is adjusted in response to adjustments of said methanol to aromatic feedstock molar ratio in (e) to maintain the conversion of methanol substantially constant.

In one embodiment, said catalyst is present as a fluidized bed of solid catalyst particles, typically comprising a porous crystalline material, such as ZSM-5 or ZSM-11, especially where the porous crystalline material has a Diffusion Parameter for 2,2 dimethylbutane of about 0.1-15 sec$^{-1}$ when measured at a temperature of 120° C. and a 2,2 dimethylbutane pressure of 60 torr (8 kPa).

DETAILED DESCRIPTION

The present invention relates to a process for producing para-xylene by alkylating an aromatic feedstock which comprises toluene and/or benzene with methanol. In the process the aromatic feedstock is preheated to a first predetermined temperature, the methanol is preheated to a second predetermined temperature and the preheated reagents are then supplied to a reactor containing an alkylation catalyst. By controlling the first and second predetermined temperatures and adjusting the molar ratio of the methanol to the aromatic feedstock, the temperature in the reactor is maintained at or near the desired optimal value thereby maximizing the selectivity of the reaction towards the desired para-xylene product.

Alkylation Process

The alkylation process employed herein can employ any aromatic feedstock comprising toluene and/or benzene, although in general it is preferred that the aromatic feed contains at least 90 weight %, especially at least 99 weight %, of benzene, toluene or a mixture thereof. An aromatic feed containing at least 99 weight % toluene is particularly desirable.

Similarly, although the composition of the methanol-containing feed is not critical, it is generally desirable to employ feeds containing at least 90 weight %, especially at least 99 weight %, of methanol.

The catalyst employed in the present process is a porous crystalline material, typically having a Diffusion Parameter for 2,2 dimethylbutane of about 0.1-15 sec$^{-1}$ when measured at a temperature of 120° C. and a 2,2 dimethylbutane pressure of 60 torr (8 kPa).

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The porous crystalline material is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the present process.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one embodiment, the zeolite employed in the process of the invention is ZSM-5 having a silica to alumina molar ratio of at least 250, as measured prior to any treatment of the zeolite to adjust its diffusivity.

Zeolite ZSM-5 and the conventional preparation thereof are described in U.S. Pat. No. 3,702,886. Zeolite ZSM-11 and the conventional preparation thereof are described in U.S. Pat. No. 3,709,979. Zeolite ZSM-12 and the conventional preparation thereof are described in U.S. Pat. No. 3,832,449. Zeolite ZSM-23 and the conventional preparation thereof are described U.S. Pat. No. 4,076,842. Zeolite ZSM-35 and the conventional preparation thereof are described in U.S. Pat. No. 4,016,245. ZSM-48 and the conventional preparation thereof is taught by U.S. Pat. No. 4,375,573. The entire disclosures of these U.S. patents are incorporated herein by reference.

The medium pore zeolites described above are preferred for the present process since the size and shape of their pores favor the production of p-xylene over the other xylene isomers. However, conventional forms of these zeolites have Diffusion Parameter values in excess of the 0.1-15 sec$^{-1}$ range desired for the present process. Nevertheless, the required diffusivity can be achieved by severely steaming the zeolite so as to effect a controlled reduction in the micropore volume of the catalyst to not less than 50%, and preferably 50-90%, of that of the unsteamed catalyst. Reduction in micropore volume is derived by measuring the n-hexane adsorption capacity of the zeolite, before and after steaming, at 90° C. and 75 ton n-hexane pressure.

Steaming of the porous crystalline material is effected at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups IIA, IIIA, IIIB, IVA, VA, VB and VIA of the Periodic Table (IUPAC version). Most preferably, said at least one oxide modifier is selected from oxides of boron, magnesium, calcium, lanthanum and most preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt. %, and preferably is between about 0.1 and about 10 wt. %, based on the weight of the final catalyst.

Where the modifier includes phosphorus, incorporation of modifier in the catalyst of the invention is conveniently achieved by the methods described in U.S. Pat. Nos. 4,356,338, 5,110,776, 5,231,064 and 5,348,643, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt. %.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3-5 hours.

Representative phosphorus-containing compounds which may be used to incorporate a phosphorus oxide modifier into the catalyst of the invention include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$ and secondary, $R_2P(O)OX$, phosphonic acids. such as benzene phosphonic acid, the corresponding sulfur derivatives such as $RP(S)(SX)_2$ and $R_2P(S)SX$, the esters of the phosphonic acids, such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphorochloridites, $(RO)PCl$, dialkylphosphinochloroidites, $R_2PCl$, alkyl alkylphosphonochloridates, $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-$P_2O_5$ reaction products.

Representative boron-containing compounds which may be used to incorporate a boron oxide modifier into the catalyst of the invention include boric acid, trimethylborate, boron oxide, boron sulfide, boron hydride, butylboron dimethoxide, butylboric acid, dimethylboric anhydride, hexamethylborazine, phenyl boric acid, triethylborane, diborane and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium bromide, magnesium hydride, magnesium lactate, magnesium laurate, magnesium oleate, magnesium palmitate, magnesium salicylate, magnesium stearate and magnesium sulfide.

Representative calcium-containing compounds include calcium acetate, calcium acetylacetonate, calcium carbonate, calcium chloride, calcium methoxide, calcium naphthenate, calcium nitrate, calcium phosphate, calcium stearate and calcium sulfate.

Representative lanthanum-containing compounds include lanthanum acetate, lanthanum acetylacetonate, lanthanum carbonate, lanthanum chloride, lanthanum hydroxide, lanthanum nitrate, lanthanum phosphate and lanthanum sulfate.

The porous crystalline material employed in the present process may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt. % of the composite.

In one embodiment, the binder material comprises silica or a kaolin day. Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

The present process can be conducted with the catalyst disposed in one or more fixed, moving or fluidized beds. Preferably, however, the catalyst particles are disposed in one or more fluidized beds. Each of the methanol and aromatic feeds can be injected into the fluidized catalyst in a single stage. However, in a preferred embodiment, the methanol feed is injected in stages into the fluidized catalyst at one or more locations downstream from the location of the injection of the aromatic reactant into the fluidized catalyst. For example, the aromatic feed can be injected into a lower portion of a single vertical fluidized bed of catalyst, with the methanol being injected into the bed at a plurality of vertically spaced intermediate portions of the bed and the product being removed from the top of the bed. Alternatively, the catalyst can be disposed in a plurality of vertically spaced fluidized catalyst beds, with the aromatic feed being injected into a lower portion of the first fluidized bed and part of the methanol being injected into an intermediate portion of the first bed and part of the methanol being injected into or between adjacent downstream catalyst beds.

Irrespective of the disposition of the catalyst, as the alkylation reaction proceeds the catalyst gradually deactivates as a result of build-up of carbonaceous material, generally referred to as "coke" on the catalyst. Thus, a portion of the catalyst in the or each alkylation reactor is generally withdrawn, either on a continuous or a periodic basis, and fed to a separate regenerator. In the regenerator, the catalyst, again preferably in the form of a fluidized bed, is contacted with an oxygen-containing gas, such as air, at a temperature between about 400 and about 700° C. so as to burn off the coke and regenerate the catalyst. The regenerated catalyst is then continuously or periodically returned to the alkylation reactor.

Process Control

Generally, the conditions employed in the present alkylation process include a temperature between about 450 and about 700° C., such as between about 550 and about 650° C.; a pressure between about 1 atmosphere and about 1000 psig (between about 100 and about 7000 kPa), such as between about 10 psig and about 200 psig (between about 170 and about 1480 kPa); a molar ratio of aromatic to methanol in the reactor charge of at least about 0.2, and preferably from about 2 to about 20; and a weight hourly space velocity ("WHSV") for total hydrocarbon feed to the reactor(s) of about 0.2 to about 1000, preferably about 0.5 to about 500 for the aromatic reactant, and about 0.01 to about 100 for the methanol reagent, based on total catalyst in the reactor(s).

More specifically, the conditions in the alkylation process are controlled so as to maximize the selectivity of the reaction to the desired para-xylene product. In general, this is achieved by maintaining the reaction temperature at a relatively high value (about 590° C.) and operating with an excess of the aromatic reagent (a molar ratio of aromatic to methanol in the reactor charge of at least 2). Normally, the alkylation conditions are substantially adiabatic, that is heat is not actively added to or removed from the alkylation reactor system. Thus all the heat required to maintain the reaction temperature at the desired value is provided by a combination of the heat initially supplied to the methanol and aromatic feeds and the exothermic heat generated in the reaction. In particular, the temperature control in the present process involves initially preheating the methanol and aromatic feeds to first and second predetermined temperatures, respectively, at or near the maximum values consistent with avoiding feed decomposition in the preheaters. In the case of the methanol feed, this involves preheating the feed to a first temperature between about 150° C. and about 300° C., such as about 220° C., whereas in the case of the aromatic feed the second temperature is between about 300° C. and about 700° C., such as about 550° C.

In addition, temperature control is effected by measuring the temperature in the alkylation reactor and comparing the measured temperature with a predetermined optimal temperature in the reactor (usually about 590° C.). The molar ratio of methanol to aromatic feedstock supplied to the reactor is then used to reduce any difference between the measured and predetermined optimal temperatures in the reactor, generally to a value to less than 10° C., typically to less than 5° C. Thus, since the conversion of methanol in the process, whether by alkylation or the production of light gases, is exothermic, any increase in the methanol to aromatic molar ratio will increase the supply of heat to the reaction and hence raise the reaction temperature. Alternatively, since conversion of methanol is the rate limiting step, any decrease in the methanol to aromatic molar ratio will decrease the supply of heat to the reaction and hence lower the reaction temperature. Controlling the reaction temperature in this manner guarantees that, for a given desired reaction temperature and maximum value of the feed preheating temperatures, the lowest possible methanol to aromatic molar ratio will be employed. This maintains the methanol concentration in the reactor at its lowest possible value, resulting in the highest possible selectivity to the desired xylene product.

For an adiabatic system, if the reactor is perfectly mixed, the temperature will be uniform throughout the reactor and all reactions will proceed at a single reaction temperature. Thus, in effecting temperature control, it is unimportant where the temperature in the reactor is measured. On the other hand, if the reactor is not perfectly mixed, or is plug flow, there will be a temperature profile across the reactor, with the highest temperature being at the reactor outlet. In this case, the reactor temperature is preferably measured at or neat the point where the reaction effluent exits the reactor.

In one embodiment of the present process, the degree of conversion of methanol is also controlled so as to remain substantially constant. This can be achieved without disturbing the reaction temperature control by adjusting the amount of catalyst in the reactor, the catalyst activity or both. Adjustment of catalyst amount and activity are easiest to effect in a fluid bed system as described above. Thus, for example, the catalyst amount can be adjusted by adding or removing catalyst from the reactor, or by shifting the amount of catalyst in the reactor versus that in the regenerator, whereas the catalyst activity can be adjusted by changing either or both of the catalyst regeneration rate and the make-up rate of fresh catalyst.

In addition to paraxylene, the process according to the present invention can be used to produce toluene (from benzene), other C7+ products such as ortho- and metaxylene, along with side products including light olefins such as ethylene, propylene, butylene isomers, pentene, hydrogen, methane, ethane, butane, pentane, butadiene, and the like. Accordingly, while the present invention is directed most specifically to the preferred embodiment of the production of paraxylene, one of skill in the art would recognize that through routine experimentation the process of the invention can be optimized for the production of one of the other products set forth herein.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for the production of para-xylene by reacting methanol with an aromatic feedstock comprising toluene and/or benzene, the process comprising:
   (a) preheating the methanol to a first temperature of between about 150° C. about 220° C.;
   (b) preheating the aromatic feedstock to a second temperature of between about 300° C. about 550° C.;
   (c) supplying the preheated methanol and the preheated aromatic feedstock to a reactor;
   (d) contacting said preheated aromatic feedstock with said preheated methanol under alkylation conditions in said reactor in the presence of a porous crystalline catalyst so that the methanol reacts with the aromatic feedstock to produce an effluent comprising para-xylene;
   (e) measuring a temperature within said reactor and comparing the measured temperature with a predetermined optimal temperature; and
   (f) adjusting the molar ratio of methanol to aromatic feedstock supplied to the reactor in (c) in a manner to reduce any difference between the measured and predetermined optimal temperatures in the reactor to less than 10° C.

2. The process of claim 1, wherein said methanol to aromatic feedstock molar ratio is adjusted to reduce the difference between the measured and predetermined optimal temperatures in the reactor to less than 5° C.

3. The process of claim 1, wherein said adjusting comprises increasing said methanol to aromatic feedstock molar ratio if the measured temperature is less than said predetermined optimal temperature.

4. The process of claim 1, wherein said adjusting comprises decreasing said methanol to aromatic feedstock molar ratio if the measured temperature is greater than said predetermined optimal temperature.

5. The process of claim 1, wherein said predetermined optimal temperature is between about 450° C. and about 700° C.

6. The process of claim 1, wherein said predetermined optimal temperature is about 590° C.

7. The process of claim 1, wherein said alkylation conditions are adiabatic.

8. The process of claim 1, wherein the amount and/or the activity of the catalyst contacting said preheated aromatic feedstock and said preheated methanol in (d) is adjusted in response to adjustments of said methanol to aromatic feedstock molar ratio in (e) to maintain the conversion of methanol substantially constant.

9. The process of claim 1, wherein said catalyst is present as a fluidized bed of solid catalyst particles.

10. The process of claim 1, wherein the porous crystalline material has a Diffusion Parameter for 2,2 dimethylbutane of about 0.1-15 sec$^{-1}$ when measured at a temperature of 120° C. and a 2,2 dimethylbutane pressure of 60 ton (8 kPa).

11. The process of claim 1, wherein the porous crystalline material comprises an aluminosilicate zeolite.

12. The process of claim 11, wherein said zeolite is ZSM-5 or ZSM-11.

13. A process comprising contacting methanol with an aromatic feedstock comprising at least one of benzene and toluene in the presence of a porous crystalline catalyst suitable for the production of paraxylene from said contacting, said process comprising:
   (a) preheating methanol to a first temperature of between about 150° C. about 220° C.;
   (b) preheating the aromatic feedstock to a second temperature of between about 300° C. about 550° C.;
   (c) supplying the preheated methanol and the preheated aromatic feedstock to a reactor;
   (d) contacting said preheated aromatic feedstock with said preheated methanol under alkylation conditions in said reactor in the presence of said catalyst so that the methanol reacts with the aromatic feedstock to produce an effluent comprising at least one xylene;
   (e) measuring a temperature within said reactor and comparing the measured temperature with a predetermined optimal temperature; and
   (f) adjusting the molar ratio of methanol to aromatic feedstock supplied to the reactor in (c) in a manner to reduce any difference between the measured and predetermined optimal temperature in the reactor to less than 10° C.

* * * * *